United States Patent
Barrett et al.

(10) Patent No.: US 6,664,380 B1
(45) Date of Patent: Dec. 16, 2003

(54) PERFLUOROSULFONYLMETHIDE COMPOUNDS; USE THEREOF FOR CARBON-CARBON BOND FORMATION

(75) Inventors: Anthony Gerard Martin Barrett, London (GB); David Christopher Braddock, London (GB); David Chadwick, London (GB)

(73) Assignee: The Institute of Applied Catalysis, London (GB)

( * ) Notice: Subject to any disclaimer, the term of this patent is extended or adjusted under 35 U.S.C. 154(b) by 0 days.

(21) Appl. No.: 10/049,832

(22) PCT Filed: Mar. 31, 2000

(86) PCT No.: PCT/GB00/03066

§ 371 (c)(1),
(2), (4) Date: Feb. 19, 2002

(87) PCT Pub. No.: WO01/12322

PCT Pub. Date: Feb. 22, 2001

(30) Foreign Application Priority Data

Aug. 18, 1999 (GB) .............................................. 9919583
Mar. 31, 2000 (GB) .............................................. 0007839

(51) Int. Cl.$^7$ .................................................. C07F 5/00
(52) U.S. Cl. ............................ 534/15; 549/220; 556/1; 556/69; 556/76; 556/182; 560/57; 560/96; 568/828; 568/832
(58) Field of Search ............................... 534/15; 556/1, 556/182, 69, 76; 560/57, 96; 568/828, 832; 549/220

(56) References Cited

U.S. PATENT DOCUMENTS 3,333,007 A * 7/1967 Scanley ........................ 568/32
5,554,664 A * 9/1996 Lamanna et al. ............. 522/25
5,728,901 A    3/1998 Ramprasad et al. ......... 568/930

FOREIGN PATENT DOCUMENTS

WO    WO 97/11930    4/1997

OTHER PUBLICATIONS

Shu Kobayashi and Shunsuke Iwamoto, "Catalytic Friedel–Crafts Acylation of Benzene, Chlorobenzene, and Fluorobenzene Using a Novel Catalyst System, Hafnium Triflate and Trifluoromethanesulfonic Acid" Apr. 24, 1998, pp. 4697–4700.

Francis J. walker, et al., Tris (trifluoromethanesulfonyl) methide Preparation, X–ray Crystal Structures, and Exceptional Catalytic Activity as a Courterion with Ytterbium (III) and Scandium (III), Jan. 20, 1998, pp. 2910–2913.

* cited by examiner

Primary Examiner—Porfirio Nazario-Gonzalez
(74) Attorney, Agent, or Firm—Morgan Lewis & Bockius LLP

(57) ABSTRACT

Free perfluorosulfonylmethide compounds and metal salts thereof show strong catalytic activity in carbon-carbon bond formation reactions, in amounts as low as 0.1 mole %. Fluorous media may be used, especially biphasic fluorous media enabling ready recycling of the catalyst. The formula thereof is: $M[C(SO_2R^1)_{3-(m+q)}(SO_2R^2)_m(SO_2R^3)_q]_x$ where M is H, Sc, Y, La, Ce, Pr, Nd, Sm Eu, Gd, Tb, Dy, Ho, Er, Tm, Yb, Lu, Zr, Hf, Th, Nb, Ta, U, Bi, Al, Ga, In or Tl, x is the common oxidation state of a said metal M, $R^1$, $R^2$ and $R^3$ are perfluorinated or polyfluoronated hydrocarbon, ether or amine moieties or mixtures thereof and m+q=0, 1, 2 or 3 (m and q being zero or integers).

22 Claims, No Drawings

//www.w3.org/1999/xlink" xmlns:xlink="http://www.w3.org/1999/xlink">

PERFLUOROSULFONYLMETHIDE COMPOUNDS; USE THEREOF FOR CARBON-CARBON BOND FORMATION

This application, filed under 35 U.S.C. 371, is the National Stage application of International Application of PCT/GB00/03066, filed Mar. 31, 2000.

The present invention relates to catalyst compounds and processes for carbon-carbon bond formation, and particularly for alkene or aromatic acylation, alkoxylation or alkylation reactions.

The most widespread of these reactions is the Friedel-Crafts reaction, the activating agents for which are relatively low cost and enable a wide variety of organic manufacturing processes. Other reactions include the Diels-Alder and Kondakov reactions.

These reactions however present the manufacturer with a number of challenges, including the handling of raw materials, the handling of solvents, process conditions and effluent control. For example, such reactions often require the use of acyl halides, Lewis acid activating agents (typically $AlCl_3$, $TiCl_4$, $BF_3$) and halogenated solvents. The handling of these can present significant health, safety and environmental problems, especially for the batch processing typically used by smaller companies or for smaller quantity production.

Also because the activating agent is typically decomplexed from the product by the use of water, there is a considerable amount of aqueous effluent generated, which must be treated to be environmentally acceptable.

Furthermore, the activating agent, although sometimes called a catalyst, is not a true catalyst since it usually has to be present in more or less stoichiometric amounts, and the decomplexing hydration effectively renders the agent non-reusable.

There have been proposals for various catalysts and processes as substitutes, and although some of these have had limited success for specific starting materials or types of starting materials, there has been no proposal of which we are aware which would be generally applicable over a wide range of starting material, which would use truly catalytic materials and quantities and which would not pose other problems as severe as those encountered in the classical Friedel-Crafts situation.

Reviewing current industrial practice in more detail, typical raw material feedstocks are (1) substituted aromatics (alkylbenzenes, tetralins, naphthalenes, thiophenes, phenols), alkenes; (2)acylating agents—acyl halides (acetyl chloride, benzoyl chloride), acyl anhydrides, epoxides (ethylene/propylene oxide) and fatty acids; (3) Lewis acids—($AlCl_3$, $TiCl_4$, $BF_3$) and (4) solvents—such as dichloroethane/methane, chlorobenzene and nitro-solvents.

A generic example is as follows:

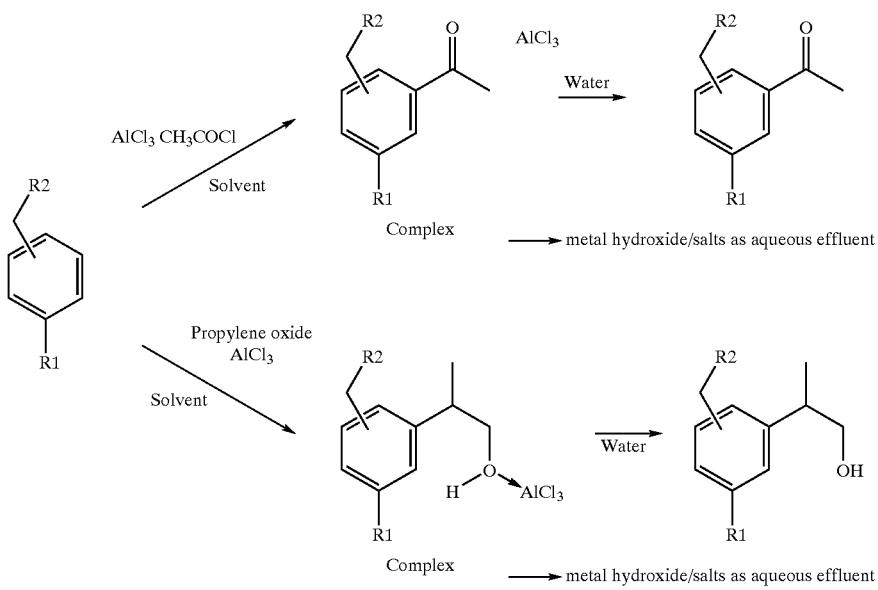

Typically, alkenes or substituted aromatics are reacted in the presence of a Lewis acid activating agent with an acyl chloride or anhydride to give ketones, or with an epoxide to give an oxalkylated product. The Lewis acid is present in at least stoichiometric amounts and the reactions nearly always require a polar solvent.

Strictly speaking the Lewis acids (typically $AlCl_3$, $TiCl_4$) used are not true catalysts as they are used in stoichiometric amounts or more. This is because they form complexes with product compounds which are more strongly bonded than with the reagents and this requires a destructive method (aqueous hydrolysis) of retrieving the product, so the Lewis acids are non-recoverable.

$AlCl_3$, $TiCl_4$ and $FeCl_3$ have the advantage of ready economic supply. Other more exotic and expensive Lewis acid catalysts are used in different parts of the chemical industry.

A Friedel-Crafts acylation reaction will end up with the product as a complex with the Lewis acid activating agent. These complexes are solids if isolated (which is unusual) but in practice the polar solvent typically employed keeps them in liquid phase and prevents potential abrasion of the reactor wall. The products are liberated by the addition of water which also reacts with the freed activating agent to generate a large volume of a non-recoverable effluent stream.

The acyl halides and Lewis acids are moisture-sensitive with the risk of liberation of hydrogen halides (usually as hydrogen chloride). Additionally, solid Lewis acids can present both dust and mechanical erosion problems. Reactions tend to be very fast and the time taken is directly related to heat removal from the plant. They are normally run in semi-batch mode to deal with their exothermicity, with efficient cooling or low boiling solvent reflux to take the required heat out of the system.

Reaction mixtures are usually quenched into water/ice to break the complex of catalyst and product. The resulting aqueous effluent has to be treated. Products are then recovered by solvent extraction, considerable washing (hence more effluent), solvent recovery and recrystallisation or distillation to purify the product, incurring relatively high energy costs.

Waste disposal for these reactions is expected to be subject to more stringent legislation, and to be a source of increasing cost. Waste disposal methods vary, but normally the major waste is precipitated metal hydroxide/salts, which goes to landfill unless an alternative use, e.g. as a flocculating agent, can be found.

Existing plant can be used for these reactions provided it is acid-resistant (especially to HCl). This generally rules out stainless steel and the ideal is glass-lined equipment.

The problems with these reactions are well known, and various solutions have been proposed—see for example Pearson & Buehler, "Friedel-Crafts Acylations with Little or No Catalyst", Synthesis, 1972, 533–542. Success has been limited, usually with a catalyst being found suitable only for one substrate/agent, or only in very specific conditions.

An ideal solution to the problems would include as many as possible of the following criteria:

1) the reaction should be truly catalytic, preferably giving desired selectivity
2) the catalyst should (a) not form a strong complex with the product (b) be recyclable (c) have no deleterious effect on the end product (d) not be limited by mass transfer problems
3) non-halogenated reagents could be used e.g. acids, esters or anhydrides
4) no solvents or only non-halogenated (preferably hydrocarbon) catalyst solvents would be preferable, though a fluorinated solvent would be acceptable if not soluble or can be rendered insoluble in or immiscible with the organic reaction phase.

Where there is no carboxy group in the product, as in alkylation, complexation will frequently not be a problem; but most of the other criteria apply.

The present invention is concerned with fluorinated sulfonyl compounds and their use in catalysis.

Nishikido et al, Synlett, 1998, 1347 have disclosed a lanthanide compound—ytterbium triflamide, Yb[N(SO$_2$C$_4$F$_9$)$_2$]$_3$—as a catalyst, which may be used in catalysis of Friedel-Crafts and Diels-Alder reactions. See also Zhu, Synthesis, 1993, 953.

WO-A-97/11930 shows Bismuth triflate, Bi(OSO$_2$CF$_3$)$_3$, as a catalyst. Kobayashi et al, Synlett 1994, 545 have demonstrated that lanthanum and hafnium triflates are catalysts for Friedel-Crafts acylation reactions.

Turowsky & Seppelt, Inorg. Chem., 1988, 27, p2135, have disclosed the preparation of HC(SO$_2$CF$_3$)$_3$.

In the Journal of Organic Chemistry 1999, 64, p2910, Waller et al disclose the compounds Yb and Sc [C(SO$_2$CF$_3$)$_3$]$_3$, as aromatic nitration catalysts. They name the compounds "triflides". They also disclose a method for their synthesis.

The present invention utilizes, to fulfil one or more of those desirable criteria listed above, the use of a fluorosulfonylmethide compound represented by the formula I:

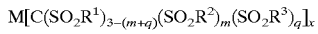

where
M is H, Sc, Y, La, Ce, Pr, Nd, Sm, Eu, Gd, Tb, Dy, Ho, Er, Tm, Yb, Lu, Zr, Hf, Th, Nb, Ta, U, Bi, Al, Ga, In or Tl x is the common oxidation state of a said metal M R$^1$, R$^2$ and R$^3$ are perfluorinated or polyfluorinated hydrocarbon, ether or amine moieties and m+q=0, 1, 2 or 3 (m and q being zero or integers) as catalyst in a C—C bond formation reaction and in particular an acylation, alkylation or alkoxylation reaction.

The compound is used in catalytic quantities, for example 10 mol % or less based on the substrate of the reaction. Amounts of 5 mol % or less are effective, down to 1 mol % or below or even 0.1 mol % or below. Quantities below 0.001 mol % are unlikely to be practical.

The compound may be hydrated, and one or more of the said groups attached to a metal M i.e. within the square brackets of Formula 1, may be different from other(s) of those groups.

The common oxidation state (x) of Sc, Y, La, Pr, Nd, Sm, Eu, Gd, Tb, Dy, Ho, Er, Tm, Yb, Lu, Bi, Al, Ga, In and Tl is +3; the common oxidation state of Zr, Hf, Ce and Th is +4; the common oxidation state of Nb and Ta is +5; the common oxidation state of U is +6. The hydration number of the metal can be between 0 and 9 depending on the preparation and pre-treatment of the catalyst, but the preferred hydration number is 0. Suitable catalysts according to the process have R$^1$, R$^2$ and/or R$^3$ groups which are perfluorinated or polyfluorinated alkyl (including cycloalkyl), ether or amine groupings where a carbon atom is bound directly to the sulfur. Preferred groups include CF$_3$, C$_4$F$_9$, C$_6$F$_{13}$, C$_8$F$_{17}$, C$_2$F$_4$C$_4$H$_9$, C$_2$F$_4$OC$_4$F$_9$, C$_2$F$_4$N(C$_4$F$_9$)$_2$.

Preferred R$^1$, R$^2$ and R$^3$ groups are perfluorinated alkyl of C$_3$ or greater of the formula C$_n$F$_{2n+1}$ where n is 2 or more, more preferably 6 or more, but preferably not more than 20. Especially effective are compounds where n=2,4, 6 or 8 and R$^1$=R$^2$ (alternatively stated, m and q are both 0). The alkyl groups may be linear, branched chain or cyclic or a combination thereof.

We also provide compounds per se of the formula I above (other than those where M=(H, Yb or Sc), and R$^1$=R$^2$=CF$_3$) especially those compounds where in the group C$_n$F$_{2n+1}$, n=2, 4, 6 or 8 and R$^1$=R$^2$. We find that these higher compounds, especially where n≧4 are particularly applicable to catalysis of the formation of C—C bonds on less reactive substrates such as toluene and xylene.

Furthermore we provide methods for the preparation of these compounds which differ from that proposed by Waller et al. We have found that if the scheme proposed by Waller et al is followed for other than CF$_3$—containing compounds, the flate rather than the desired flide is obtained.

We therefore provide a method for the preparation of compounds of the formula I, other than these where R$^1$=R$^2$=R$^3$=CF$_3$ which includes the step of separating the desired flide as its alkali metal salt, usually its Lithium salt, from the analogue triflate salt by separation out of aqueous solution rather than by precipitation as in Waller et al.

We follow the nomenclature " - - - flide" for the compounds of the formula I given and defined above. For example, where n=1 they are "triflides" and where n=4, "nonaflides". We have found that these compounds, especially where n=4, 6 or 8, are more acidic and more generally applicable catalysts than triflates or triflamides. They have, moreover, the advantage that they are for the most part usable in a fluorous phase and in particular in a biphasic fluorous system (Horvath et al, Science 1994, 266, 72): this is believed to be due to the high fluorine content in these long-chain "ponytails".

Biphasic operation allows for a particularly simple and efficient recycling of catalyst.

The C—C bond formation process can be conducted at any combination of temperatures and pressures at which the process proceeds to form the desired product, e.g. an acyl arene. Reaction conditions suitable for practising the present invention will vary depending upon the arene, the acylating agent, the solvent and the catalyst according to the process. The rate of formation of the acyl arene will depend on the concentrations of arene, acylating agent, catalyst and the temperature.

Acylating agents to be used in the present process have the general structure RCOX where X is either Cl, OH or OCOR (i.e. acid anhydride) and R represents alkyl or aryl substituents. Preferred acylating agents according to the present process are acetic anhydride, acetic acid, benzoic anhydride, benzoic acid, isobutyric anhydride, isobutyric acid, pivalic anhydride, pivalic acid, propionic anhydride and propionic acid. Mixed anhydrides may be used. The acylation may also be of intramolecular nature and the preferred acylating agent is then a pendant carboxylic acid to form variously 5, 6 or 7 membered rings.

Alkoxylating agents include alkane epoxides.

Arenes capable of being treated according to the present process are those containing at least one aromatic ring; the word "aromatic" refers to an unsaturated cyclic system well understood by those in the art. A representative summary of arenes capable of undergoing acylation is presented in Advanced Organic Chemistry, 4th Edition, Wiley-Interscience, 1992. Such arenes include benzene, substituted benzenes, fused aromatics where the arene is naphthalene, anthracene, phenanthrene and their derivatives, aromatic heterocycles such as furan, pyrrole, thiophene and their derivatives. Acylation of arenes more deactivated than monohaloarenes is currently not possible, where "deactivated" is a measure of reactivity well understood by those in the art Arenes which possess a single aromatic benzenoid ring are represented by Formula A.

Formula A

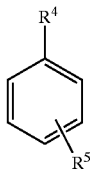

wherein $R^4$ and $R^5$ are independently selected from a hydrogen atom, a primary, secondary or tertiary alkyl having from 1 to 6 carbon atoms, a benzene ring or fused ring, which may be substituted, and a halide (i.e. fluoride, chloride, bromide or iodide) and u is zero or an integer which is 1 to 4 with the proviso that if $R^4$ or any $R^5$ is halide then other $R^5$ or $R^4$ cannot be halide, $OCH_3$, $OC_2H_5$, $OC_3H_7$, OPh or $NHCOCH_3$.

Preferred arenes according to Formula A include benzene, toluene, ethylbenzene, t-butylbenzene, chlorobenzene, anisole, acetanilide, biphenyl, m-xylene, p-xylene, cumene, bi and multicyclic and fused-ring aromatics such as naphthalenes and anthracenes.

Arenes to be treated according to the present process include heteroaromatics examples of which are furan, thiophene and pyrrole and substituted derivatives of these.

The arenes can be subjected to the present process to form the corresponding acyl or alkoxy arene in the appropriate position according to the theory of electrophilic substitution well understood by those in the art. Those of skill in the art can readily identify those arenes which are capable of being converted to valuable commercial products using the claimed process.

Acylated arenes of particular interest made by the claimed process are acetophenone, p-chloroacetophenone, p-methoxyacetophenone and 2-acetylthiophene and 4-isobutyroyltoluene.

The C—C bond formation catalysed may be intramolecular, including cyclisation and hydroxyalkylation.

As has already been noted, a solvent may be used in the present process although the arene, other substrate and/or other reactive component may serve as the reaction medium. Preferred processes employ a solvent. Suitable solvents for practising the current process include any solvent or mixture of solvents wherein the solvent is inert with respect to the reactants under the particular process conditions. The term "inert" means that the solvent will not react with any other component of the reaction mixture: the arene, the acylating agent, the catalyst, the product and the side-product. Many solvents can be used including selected hydrocarbons, chlorinated hydrocarbons and other solvents. Examples are dichloromethane, 1,2-dichloroethane and benzotrifluoride. In the most preferred process, the solvent is fluorous and examples include perfluoromethyldecalin, perfluoroheptane, perfluoromethylcyclohexane and FC-88.

When no other material is added as solvent, the catalyst compound may subsequent to completion of the reaction be removed by preferential transfer into a solvent for that compound, e.g. a fluorous medium.

The following examples are given by way of illustration.

PROCESS EXAMPLES

Example 1

The present catalysts were compared with triflate and triflamide compounds in an "easy" acylation of anisole, in the presence of nitromethane or benzo trifluoride ("BTF") at room temperature under an inert atmosphere. Throughout, comparative experiments are marked with an asterisk*, RT=Room Temperature, and volume of nitromethane or BTF is 1 ml unless otherwise stated.

First, a compound of formula I wherein m and q are zero, M=Yb and n=1 i.e. Tf=$(SO_2CF_3)$ was tested, with the reaction schemes given below and results given in Tables 1 & 2 respectively.

The catalyst was recovered by concentration of the final reaction mixture under vacuum, dissolution of the residue in dichloromethane, and extraction of the catalyst with water. The catalyst separated as a solid when the combined aqueous extracts were evaporated. Acetic anhydride was selected as the acylating agent and anisole was employed as the substrate.

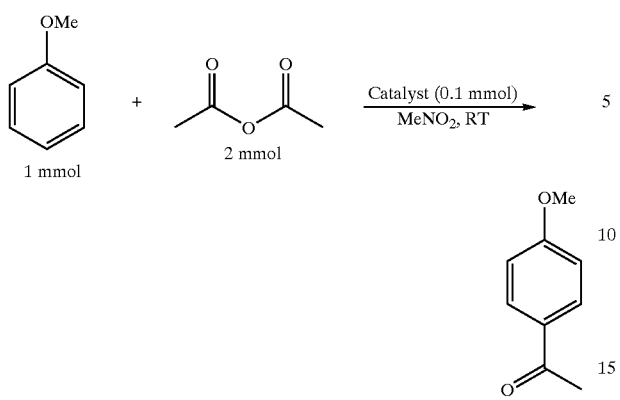

TABLE 1

| | Catalyst/% yield | | |
|---|---|---|---|
| Time (hours) | Yb (OTf)₃* | Yb (NTf₂)₃* | Yb (CTf₃)₃ |
| 1 | 22 | 74 | 68 |
| 2 | 31 | 82 | 76 |
| 3 | 35 | 85 | 78 |
| 4 | 41 | 87 | 80 |
| 18 | 57 | 95 | 90 |
| Catalyst Recovery (%) | 96 | 94 | 89 |

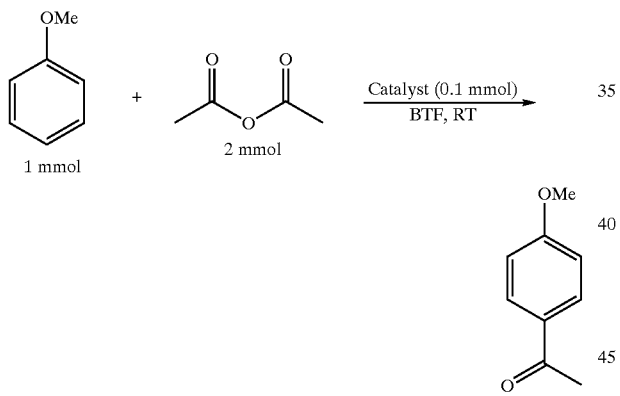

TABLE 2

| | Catalyst/% yield | | |
|---|---|---|---|
| Time (hours) | Yb(OTf)₃* | Yb(NTf₂)₃* | Yb(CTf₃)₃ |
| 1 | 7 | 29 | 29 |
| 2 | 9 | 38 | 42 |
| 3 | 12 | 43 | 49 |
| 4 | 14 | 48 | 54 |
| 18 | 29 | 71 | 77 |
| Catalyst Recovery (%) | 95 | 95 | 93 |

Both activity and recovery figures for the present compounds are very satisfactory.

Then, catalysts wherein $C_nF_{2n+1}$ where n=4 i.e. Nf=$(SO_2C_4F_9)$, n=6 i.e. Tdf=$(SO_2C_6F_{13})$ and 8 i.e. Hdf=$(SO_2C_8F_{17})$ were compared with n=1 and the analogue triflamide compound—see Table 3. Results for $Yb(NTf_2)_3$ and $Yb(CTf_3)_3$ from Table 2 are repeated in Table 3.

These examples used benzotrifluoride (BTF) as the solvent. Although BTF does not display fluorous phase behaviour, it is a useful hybrid between classical organic solvents and perfluorinated (i.e. fluorous) solvents.

TABLE 3

| | Catalyst/% yield | | | | |
|---|---|---|---|---|---|
| Time (Hours) | Yb (NTf₁)₃* | Yb (CTf₃)₃ | Yb (CNf₃)₃ | Yb (CTdf₃)₃ | Yb {C(Tdf)₂Hdf}₃ |
| 1 | 29 | 29 | 48 | 55 | 19 |
| 2 | 38 | 42 | 53 | 62 | 32 |
| 3 | 43 | 49 | 59 | 67 | — |
| 4 | 48 | 54 | 63 | 74 | 48 |
| 18 | 71 | 77 | 86 | — | 73 |

The results seen in Tables 2 and 3 clearly show that the first three methide complexes are significantly superior to ytterbium triflate or ytterbium triflamide and are increasingly effective with increasing fluorine content. Surprisingly, the fourth catalyst, with the highest fluorine content (129 F/Yb), was found to be the least active of the methide complexes. It is reasonable to speculate that the high fluorine content renders it less well suited to the non-fluorous solvent BTF and hence shows lower catalytic activity—but see Example 4 below.

Example 2

The present triflide $Yb(CTf_3)_3$ was then compared to the corresponding triflamide in acylation of a less reactive substrate—toluene. Results are seen in Table 4.

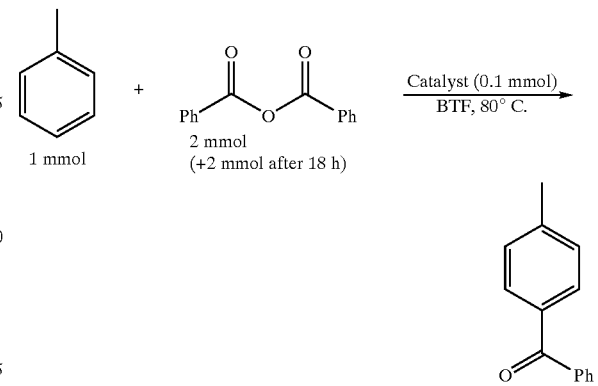

TABLE 4

| Time (hours) | Catalyst/% yield | |
|---|---|---|
| | Yb (Ntf$_2$)$_3$* | Tb (CTf$_3$)$_3$ |
| 4 | 0 | 6 |
| 18 | 2 | 25 |
| 22 (18 + 4) | 4 | 35 |
| 66 (18 + 48) | 24 | 74 |

As can be seen, the results given by the present compound are strikingly superior.

Example 3

Present compounds Yb(CTf$_3$)$_3$ and Yb(CNf$_3$)$_3$ were employed for the acylation of various arene substrates in BTF using acetic anhydride or benzoic anhydride. In all cases the more fluorinated nonaflide catalyst was found to be more active—Table 5.

TABLE 5

Catalytic Friedel-Crafts Acylation of Arenes

| Catalyst[a] | Arene | T/° C. | % Conversion[b] |
|---|---|---|---|
| Triflide[c] | Thiophene | room temp | 60 |
| Nonaflide[c] | Thiophene | room temp | 76 |
| Triflide[d] | Toluene | 80 | 35 |
| Nonaflide[d] | Toluene | 80 | 41 |
| Triflide[d] | Naphthalene | 102 | 94 |
| Nonaflide[d] | Naphthalene | 102 | 95 |
| Triflide[c] | m-xylene | 80 | 19 |
| Nonaflide[c] | m-xylene | 80 | 22 |

[a]All reactions run with 2 equivalents of anhydride, 10 mol % of catalyst with respect to the arene substrate in BTF for 18 h.
[b]Determined by Gas Chromatographic Mass Spectrometry (GCMS) analysis.
[c]Acetic anhydride employed.
[d]Benzoic anhydride employed.

Example 4

The solubility of the various catalysts in the fluorous solvent perfluoromethyldecalin (PMD) (b.p. ca. 150° C.) was examined. While ytterbium triflate, triflamide and triflide were all found to be insoluble in refluxing PMD, both ytterbium nonaflide and tridecaflide salts were found to be soluble at reflux. Most encouragingly, the mixed tridecaflide and heptadecaflide was found to be fully soluble at 80–90° C.; however, neither were soluble at room temperature.

The general procedure for the acylation reactions was as follows:

To a stirred mixture of catalyst (10 mol %) in PMD was added substrate (1 eq.) and anhydride (2 eq.). The reaction was cooled to room temperature, diluted by the addition of dichloromethane and analysed by GCMS. The reaction mixture was then extracted with hot PMD (ca 85° C.) and the combined fluorous extracts concentrated in vacuo to yield the recovered catalyst.

Specifically, attempted fluorous phase acylation of anisole with acetic anhydride in PMD (1 ml) with nonaflide catalyst at 110° C. for 2 h led to an extremely dark mixture and a 69% conversion to the acylated product was obtained. In this reaction the catalyst could not be efficiently recovered via a hot fluorous extraction regime. In contrast, use of the highly fluorinated mixed-ligand catalyst under identical conditions led to an 82% conversion to the ketone adduct. Furthermore, that mixed-ligand catalyst was recovered in 96% yield by extraction of the reaction mixture with hot (ca. 85° C.) PMD. In the second run with recycled catalyst 77% conversion to the acylated adduct was obtained. So, whilst the catalyst performed comparatively poorly in a non-fluorous system, Table 3, it is highly active in a fluorous system.

Example 5

Next, the effects if any of variation in catalyst loading were investigated under conditions similar to those of Example 4. The catalyst was Yb(C(Tdf$_x$)$_2$ Hdf)$_3$, and all runs except 5 were performed at a theoretical 0.5M concentration of anisole in PMD. The results are seen in Table 6. Note that run 5 is performed in the absence of additional solvent with very satisfactory results. The higher conversion in comparison to run 4 may be caused by the higher concentration of catalyst due to the absence of diluent solvent.

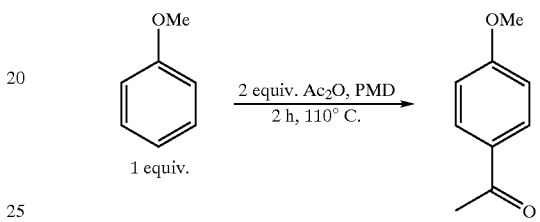

TABLE 6

| Run | mol % catalyst | % conversion[b] |
|---|---|---|
| 1 | 10 | 74 |
| 2 | 1 | 72 |
| 3 | 0.5 | 65 |
| 4 | 0.1 | 40 |
| 5 | 0.1c | 58 |
| 6* | 0 | 0 |

GCMS analysis
No solvent

Similar results are obtained upon similar reductions in concentration of other of the present compounds.

Example 6

The ability of the tris-(perfluoroalkanesulfonyl)methanes wherein n=4 and 6 respectively, to catalyse the Friedel-Crafts acylation of anisole was also investigated, in comparison to the lanthanide compounds above. The results indicated that the nonaflide (n=4) acid had a similar catalytic ability to ytterbium nonaflide at the same loading. However, increasing the fluorine content of the acid to the tridecaflide (n=6) acid had little additional catalytic effect—Table 7, unlike that observed upon going from ytterbium nonaflide to tridecaflide—see Table 3.

TABLE 7

| Time (Hours) | Nf$_3$CH-10 mol % | Nf$_3$CH-20 mol % | Tdf$_3$CH-10 mol % |
|---|---|---|---|
| 1 | 43 | 62 | 42 |
| 2 | 50 | 64 | 46 |
| 4 | 51 | 69 | 52 |
| 18 | 81 | 85 | 83 |

Examples 7 & 8

These show catalysis of intramolecular C—C bond reactions, a cyclisation and a hydroxyalkylation. All results were obtained by GCMS.

Example 7

Intramolecular carbonyl ene reaction of citronellal to isopugelone.

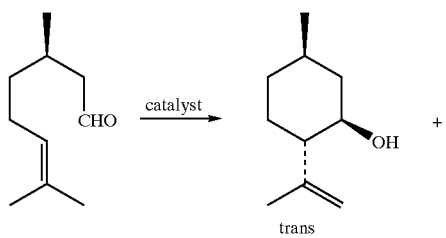

Results are seen in Table 8:

| Catalyst | Loading | Solvent (Conc.) | Time/h | Temp/° C. | % citronellal | % trans:cis:other[b] |
|---|---|---|---|---|---|---|
| Sc(OTf)$_3$* | 10 mol % | CH$_2$Cl$_2$ (0.5 M) | 1 | −78 | <1 | 62:10:38 |
| Yb(CNf$_3$)$_3$ | 1 mol % | BTF (0.5 M) | 18 | −20 | <1 | 14:4:72 |
| Yb(CNf$_3$)$_3$ | 5 mol % | CH$_2$Cl$_2$ (0.1 M) | 1 | −78 | 7 | 51:15:27 |
| Yb(CNf$_3$)$_3$ | 10 mol % | CH$_2$Cl$_2$ (0.5 M) | 18 | −78-RT | <1 | 63:21:9 |

[b]"Other" refers to dimeric by-products formed by intermolecular reaction.

Example 8

Intramolecular hydroxyalkylation of phenethyl alcohol with formalin, to isochroman.

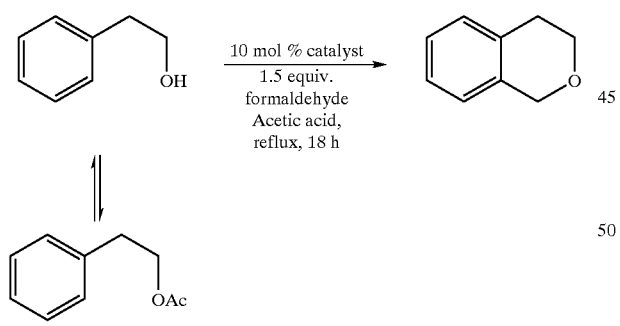

Results are seen in Table 9:

| Catalyst | Time/h | % product | % acetate |
|---|---|---|---|
| Sc(OTf)$_3$* | 0.5[b] | 33 | 66 |
| Sc(OTf)$_3$* | 4 | 78 | 22 |
| Sc(OTf)$_3$* | 18 | >95 | trace |
| Yb(CNf$_3$)$_3$ | 0.5[b] | 39 | 60 |
| Yb(CNf$_3$)$_3$ | 4 | 80 | 20 |
| Yb(CNf$_3$)$_3$ | 18 | >95 | trace |

[b]No starting alcohol is left after 0.5 and is not detected during the rest of the reaction.

Example 9

Hydroxyalkylation of anisole with ethyl glyoxalate.

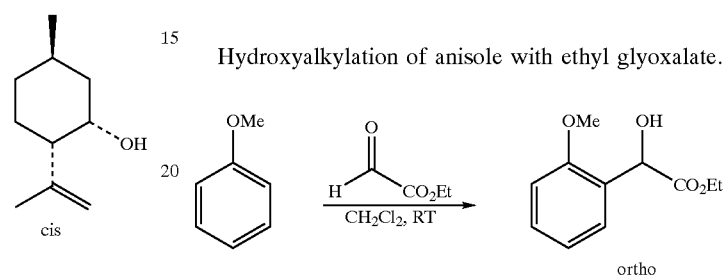

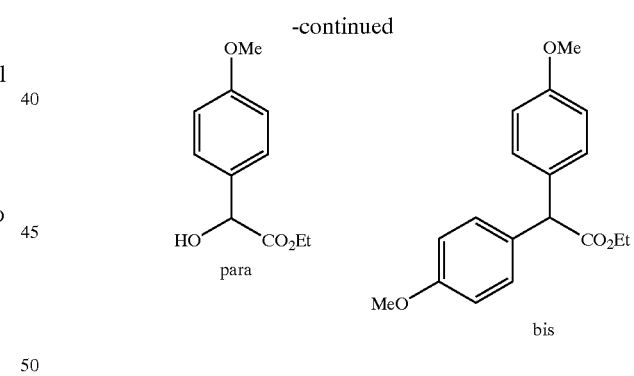

Hydroxylalkylations were carried out at a loading of 1 mol % of catalyst based on the anisole. Results obtained by GCMS, and shown in Table 10, illustrate the quicker and higher conversions achieved by use of the present compounds.

TABLE 10

| Catalyst | Time/h | unreacted anisole % | ortho % | para % | bis % |
|---|---|---|---|---|---|
| Yb(CNf$_3$)$_3$ | 1 | 80 | <1 | 17 | 3 |
| Yb(CNf$_3$)$_3$ | 2 | 70 | <1 | 22 | 7 |
| Yb(CNf$_3$)$_3$ | 18 | 31 | 8 | 22 | 38 |
| Yb(CNf$_3$)$_3$ | 48 | 9 | 8 | 6 | 76 |
| Sc(OTf)$_3$* | 1 | >99 | — | — | — |
| Sc(OTf)$_3$* | 2 | >99 | — | — | — |

TABLE 10-continued

| Catalyst | Time/h | unreacted anisole % | ortho % | para % | bis % |
|---|---|---|---|---|---|
| Sc(OTf)$_3$* | 18 | 71 | <1 | 28 | — |
| Sc(OTf)$_3$* | 48 | 57 | 9 | 40 | 2 |

Example 10

Friedel-Crafts Alkylation of Anisole with Benzhydrol

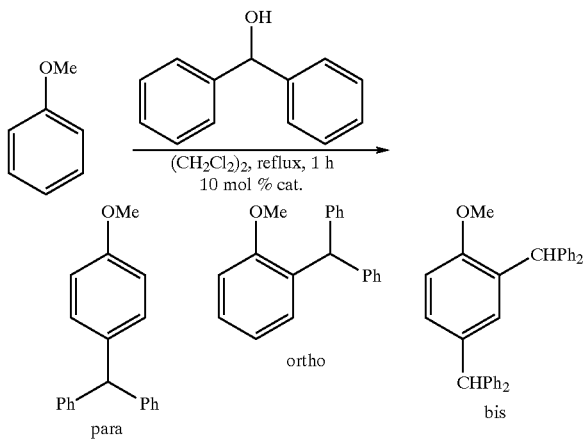

To a solution of benzhydrol (184 mg, 1.0 mmol) and anisole (543 μl, 5.0 mmol) in dry dichloroethane (5 mL) was added Yb(CNf$_3$)$_3$ (276 mg, 0.1 mmol, 10 mol %). The mixture was stirred at reflux for 1 hour. The mixture was allowed to cool, diluted with CH$_2$Cl$_2$, washed with water, dried over MgSO$_4$ and evaporated under reduced pressure. The excess anisole was removed under high vacuum at room temperature and the residue chromatographed (9:1 PE:Et$_2$O) to give the alkylation products as a mixture of inseparable ortho and para isomers (259 mg, 91%) as a colourless oil. major (para) isomer: $\delta_H$ (300 MHz, CDCl$_3$) 7.38–7.16 (10H, m, Ar—H×10), 7.10 (2H, d, J=8.5 Hz, MeO—Ar—H×2) 6.89 (2H, d, J=8.5 Hz, MeO—Ar—H×2), 3.84 (3H, s, OMe). MS 274 (M$^+$), 243, 197, 165, 153. minor (ortho) isomer: MS 274, 259, 243, 165. bis-isomer (9%): MS 440 (M$^+$), 363, 273, 165, 91.

Example 11

Resorcinarene Formation

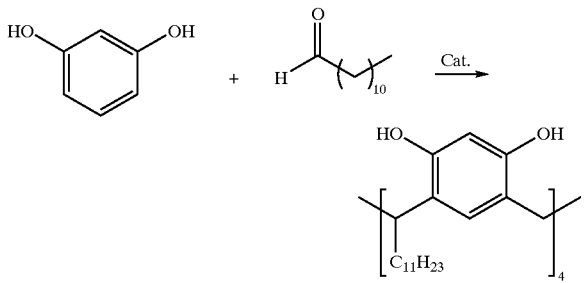

To a solution of resorcinol (33 mg, 0.3 mmol) and dodecanal (55 mg, 0.3 mmol) in absolute EtOH (0.6 mL) was added Yb(CNf$_3$)$_3$ (82 mg, 0.03 mmol, 10 mol %). The solution was stirred under reflux for 48 hours. The mixture was allowed to cool and was poured into distilled water (5 mL) and the precipitated resorcinarene was washed three times with distilled water (2 mL each), filtered and dried to constant weight in vacuo to give the product (85 mg, 100%) as a cream solid: IR (DRIFTS; KBr disk) 3300 br, 2927, 2853, 1615, 1503 cm$^{-1}$. $\delta_H$ (300 MHz, CD$_3$COCD$_3$) 8.7 (8H, br s, OH) 7.55 (4H, s, Ar—H), 6.15 (4H, s, Ar—H), 4.25 (4H, t, J=7.3 Hz, ArCH), 2.27 (2H, br s, ArCHCH$_2$)), 1.27 (18H, br s, alkyl chain CH$_2$s) 0.88 (3H, J=6.6 Hz, CH$_3$).

EXPERIMENTAL

GENERAL EXPERIMENTAL

All solvents and reagents were purified by standard techniques as reported in Perrin, D. D.; Armarego, W. L. F., Purification of Laboratory Chemicals, 3rd edition, Pergamon Press, Oxford, 1988 or used as supplied from commercial sources as appropriate. 40–60 Petroleum ether (40–60 P.E.) refers to the fraction of light petroleum ether which boils between 40–60° C. DCM, Et$_2$O and MeOH refer to dichloromethane, diethyl ether and methanol respectively. Solvents were removed under reduced pressure using a Büchi R110.

Infrared spectra were recorded using Mattson 500 fourier transform spectrometer with major absorbances only being quoted.

$^1$H NMR spectra were recorded at 250, 300 and 400 MHz using Bruker AM-250, Bruker DRX-300 and Bruker DRX-400 instruments. For $^1$H spectra recorded in CDCl$_3$, d$_6$-DMSO and (CD$_3$)$_2$CO, chemical shifts are quoted in parts per million (ppm) and are referenced to the residual solvent peak. The following abbreviations are used: s, singlet; d, doublet; t, triplet; q, quartet; m, multiplet; br, broad.

$^{13}$C NMR spectra were recorded at 75 and 100 MHz using Bruker DRX-300 and Bruker DRX-400 instruments. Chemical shifts are quoted in ppm.

$^{19}$F NMR spectra were recorded at 250 MHz using a Bruker AM-250 instrument. Chemical shifts are quoted in ppm.

Low resolution mass spectra were obtained at the Imperial College of Science, Technology and Medicine Department of Chemistry Mass Spectrometry Service, with modes of ionisation being indicated as CI or FAB and with only molecular ion, molecular ion fragments and major peaks being reported.

Single crystal X-ray structures were determined by the Imperial College Department of Chemistry, X-ray Laboratories.

Flash chromatography was carried out using BDH 40–63 μM grade silica as stationary phase. Thin layer chromatography was carried out on glass backed plates pre-coated with Merck silica gel 60 F$_{254}$ which were visualised by quenching of u.v. fluorescence or by staining with ceric molybdate (followed by heat) as appropriate.

Bulb to bulb distillation/sublimation was carried out using a Kugelrohr distillation apparatus with the collection bulb cooled with cardice. The temperatures quoted are oven temperatures and are approximate.

Unless otherwise stated all preparative reactions were carried out under anhydrous conditions and an inert atmosphere.

EXPERIMENTAL PROCEDURES

PREPARATIVE EXAMPLES

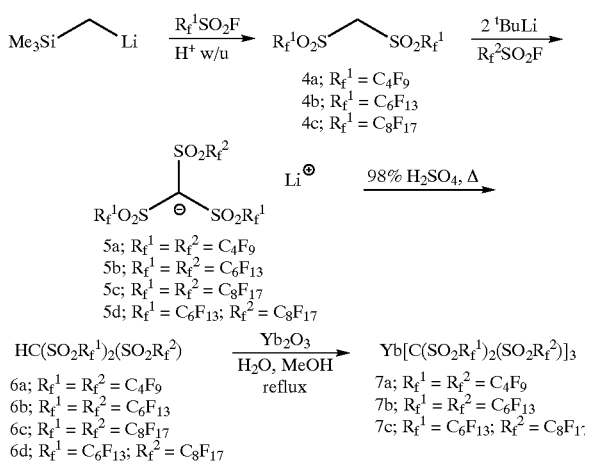

Trimethylsilylmethyllithium was added smoothly to the commercially available nonafluorobutanesulfonyl, tridecafluorohexanesulfonyl and heptadecafluorooctanesulfonyl fluorides to provide the corresponding methylene compounds 4a–c in 58%, 39% and 29% yields respectively (Scheme 1). Owing to significant changes in solubility as the fluorine content increases along the series 4a to 4c modified work-up procedures were adopted for their isolation. The corresponding $C_4$ ("nonaflide"), $C_6$ ("tridecaflide") and $C_8$ ("heptadecaflide") methide lithium salts 5a–c were obtained by double deprotonation with tert-butyllithium and quenching with the respective sulfonyl fluorides (71%, 72%, 15% yield respectively). Additionally the mixed $C_6/C_8$ methide lithium salt 5d was obtained by quenching the dianion of methylene compound 4b with $C_6F_{13}SO_2F$ (49% yield). The separation procedure of Waller et al, loc cit, using cesium chloride to precipitate the flide while successful for triflides was not so for higher homologues.

The free acids 6a–d were obtained via vacuum-sublimation of 5a–d from 98% sulfuric acid (95%, 94%, 72%; 95% yields respectively) and the ytterbium catalysts 7a–b,d were readily prepared in essentially quantitative yield (96%, 100%, 98%) by the action of the free acids 6a–b,d on ytterbium oxide in water-methanol (1:1 v/v) at reflux for 24 h, followed by evaporation and drying under high-vacuum for 48 h.

Other metal M salts can be prepared similarly, if necessary after acidification of a lithium or other alkali metal salt.

A. LIGAND PREPARATIONS bis-(Nonafluorobutanesulfonyl)methane 4a, $Nf_2CH_2$

To a cooled, 2–5° C., stirred solution of trimethylsilylmethyllithium (150 mL, 150 mmol, 1M solution in pentane) was added neat nonafluorobutanesulfonyl fluoride (13.5 mL, 75 mmol) dropwise, through 1 hour by means of a syringe pump. The mixture was then stirred for 60 hours whilst allowing to warm to room temperature, before being quenched by the addition of saturated aqueous sodium bicarbonate solution (150 mL). The pentane layer was separated and the aqueous layer extracted with DCM (3×50 mL). The aqueous layer (containing a semi-solid foam) was then acidified, to pH 1, by the addition of concentrated HCl (ca 60 mL) and extracted with diethyl ether (3×50 mL). The organic extract was then dried over $MgSO_4$, filtered and concentrated in vacuo to give a brown solid which was then triturated with 40–60 P.E. (3×100 mL) to give 4a as a pale yellow solid (13.9 g, 50%). Purification by vacuum sublimation then allowed 4a to be isolated as a white powdery solid (12.7 g, 58%); $v_{max}$ (KBr)/$cm^{-1}$ 3000, 2928, 1389, 1354, 1296, 1218, 1185, 1140, 1113, 1032, 814, 722, 693; $\delta_H$ (400 MHz, $CD_3COCD_3$) 6.43 (br s, $CH_2$); $\delta_C$ (100 MHz, $CD_3COCD_3$) 66.9 (br s, $\underline{C}H_2$), 106.4–122.2 [m, ($\underline{C}_4F_9SO_2)_2C$]; $\delta_F$ (250 MHz, $CD_3COCD_3$) −125.6 (4F, m), −120.7 (4F, m), −109.5 (4F, m), −80.7 (6F, m); m/z (FAB, −ve) 579 (M−H⁺, 100%).

Lithium tris-(Nonafluorobutanesulfonyl)methide 5a, $Nf_3CLi$

To a cooled, −20° C., solution of 4a (1.16 g, 2.0 mmol) in diethyl ether (40 mL) was added dropwise tert-butyllithium (3.0 mL, 4.2 mmol, 1.4M solution in pentane) and the reaction left to stir at −20° C. for 1 hour. Nonafluorobutanesulfonyl fluoride (540 μL, 3.0 mmol) was then added dropwise. The reaction mixture was stirred for 24 hours and allowed to warm to room temperature before being concentrated in vacuo and quenched.with saturated aqueous sodium bicarbonate solution (100 mL). The aqueous layer was then acidified, to pH 1, by the addition of concentrated hydrochloric acid (ca 50 mL) before being extracted with dichloromethane (3×30 mL) followed by diethyl ether (3×30 mL). The combined ethereal extracts were then concentrated in vacuo to yield a pale yellow oil which was taken into water (10 mL). A dense yellow/brown oily layer formed which was isolated by decanting off the aqueous layer and then further washed with water (2×10 mL) before being separated. Upon standing the oil solidified into oily crystalline solid to yield 5 (1.15 g, 71%); $v_{max}$ (thin film)/$cm^{-1}$ 3534, 1378, 1352, 1239, 1214, 1162, 1142, 1123, 1029, 972, 799, 737; $\delta_C$ (100 MHz, DMSO-$d_6$) 88.7 [s, ($C_4F_9SO_2)_3\underline{C}$], 105.4–121.1 [m, ($\underline{C}_4F_9SO_2)_3C$]; $\delta_F$ (250 MHz, DMSO-$d_6$) −125.0 (6F, m), −120.6 (6F, m), −107.4 (6F, m), −79.8 (9F, m); m/z (FAB, −ve) 861 [($NF_3C)^−$, 100%].

tris-(Nonafluorobutanesulfonyl)methane 6a, $Nf_3CH$

To 5a (1.56 g, 1.8 mmol) was added concentrated $H_2SO_4$ (1.0 mL, ca 10 eq.). The resulting mixture was subjected to vacuum distillation (0.4 mbar, 150–155° C.) which generated a while oily solid. This was then dissolved in ether (10 mL) and water added (10 mL) followed by saturated aqueous barium chloride solution (20 mL). The ethereal layer was separated and the aqueous layer extracted with diethyl ether (2×15 mL). The combined ethereal extracts were then concentrated in vacuo and the organic residue subjected to vacuum distillation to yield 6a (1.48 g, 95w) as a white solid; $\delta_C$ (100 MHz, DMSO-$d_6$) 88.8 [s, ($C_4F_9SO_2)_3\underline{C}H$], 107.8–121.2 [m, ($\underline{C}_4F_9SO_2)_3CH$]; $\delta_F$ (250 MHz, DMSO-$d_6$) −125.0 (6F, m), −120.6 (6F, m), −107.3 (6F, m), −79.8 (9F, m); m/z (FAB, −ve) 861 [($Nf_3C)^−$, 100%].

bis-(Tridecafluorooctanesulfonyl)methane 4b, $Tdf_2CH_2$

To a cooled, 2–5° C., stirred solution of trimethylsilylmethyllithium (50 mL, 50 mmol), 1M solution in pentane) was added neat tridecafluorohexanesulfonyl fluoride (5.74 mL, 25 mmol) dropwise, through 2 hours by means of a syringe pump. The mixture was then stirred for 60 hours whilst allowing to warm to room temperature, before being quenched by the addition of saturated aqueous sodium bicarbonate solution (60 mL). The resulting mixture was decanted into a separating funnel, leaving a brown 'sticky' solid in the reaction vessel, the pentane layer separated and the aqueous layer extracted with DCM (3×30 mL). The aqueous layer was then acidified, to pH 1, by the addition of concentrated HCl (ca 30 mL) and extracted with diethyl ether (3×30 mL). The reaction residue was then treated and forcibly mixed with, saturated aqueous sodium bicarbonate solution (60 mL) to give a cloudy suspension. The aqueous mixture was then acidified, to pH 1, by the addition of HCl (ca 30 mL) to give a slurry which was then extracted with diethyl ether (3×30 mL). The combined ethereal extracts were then dried over $MgSO_4$, filtered and concentrated in vacuo to give a brown solid which was triturated with DCM to give 4b as a crude pale yellow solid (5.6 g, 57%). Purification by vacuum sublimation (160–170° C., 1 mbar) then allowed 4b (3.8 g, 39%) to be isolated as a white powdery solid; $\delta_H$ (400 MHz, DMSO-$d_6$) 7.34 (2H, s, C$\underline{H}_2$); $\delta_C$ (100 MHz, DMSO-$d_6$) 59.8 [s, $(C_6F_{13}SO_2)_2\underline{C}H_2$], 106.3–121.8 [m, ($\underline{C}_6F_{13}SO_2)_2CH_2$]; $\delta_F$ (400 MHz, DMSO-$d_6$) −125.1 (4F, m), −121.9 (4F, m), −121.0 4F, m), −119.1 (4F, m), −113.1 (4F, m), −79.7 (6F, m); m/z (FAB, −ve) 1239 (100%), 779 (M−H$^+$, 706).

Lithium tris-(Tridecafluorohexanesulfonyl)methide 5b, Tdf$_3$CLi

To a cooled, −20° C., solution of 4b (1.56 g, 2.0 mmol in diethyl ether (40 mL) was added dropwise tert-butyllithium (2.5 mL, 4.2 mmol, 1.7M solution in pentane) and the reaction left to warm to −20° C. over 1 hour. Tridecafluorohexanesulfonyl fluoride (689 µL, 3.0 mmol) was then added dropwise. The reaction mixture was allowed to warm to room temperature and stirred for 24 hours before being concentrated in vacuo and quenched with saturated aqueous sodium bicarbonate solution (50 mL). The aqueous layer was then acidified, to pH 1, by the addition of concentrated hydrochloric acid (ca 30 mL) before being extracted with diethyl ether (3×30 mL). The combined ethereal extracts were then concentrated in vacuo to yield a pale yellow solid which was taken into water (20 mL). A yellow/brown precipitate formed which was isolated by filtration and then washed with water (2×20 mL). Purification was then carried out by trituration with diethyl ether at −78° C. to yield 5b (1.68 g, 72%); as a brown oily solid; $\delta_C$ (100 MHz, DMSO-$d_6$) 88.7 [s, $(C_6F_{13}SO_2)_3\underline{C}$], 107.4–120.9 [m, ( $\underline{C}_6F_{13}SO_2)_3C$]; $\delta_F$ (400 MHz, DMSO-$d_6$) −125.5 (6F, m), −122.3 (6F, m), −121.2 (6F, m), −119.8 (6F, m), −107.3 (6F, m) −80.0 (9F, m); m/z (FAB, −ve) 1161 [(Tdf$_3$C)$^−$, 100%].

tris-(Tridecafluorobutanesulfonyl)methane 6b, Tdf$_3$CH

To 5b (1.65 g, 1.4 mmol) was added concentrated $H_2SO_4$ (0.75 mL, ca 10 eq.). The resulting mixture was subjected to vacuum distillation (0.35 mbar, 150–155° C.) which generated a white oily solid. This was then dissolved in ether (10 mL) and water added (10 mL) followed by saturated aqueous barium chloride solution (20 mL). The ethereal layer was separated and the aqueous layer extracted with diethyl ether (2×15 mL). The combined ethereal extracts were then concentrated in vacuo and the organic residue subjected to vacuum distillation to yield 6b (1.52 g, 94%) as a colourless oil which solidified upon standing; $\delta_F$ (250 MHz, DMSO-$d_6$) −125.4 (6F, m), −122.2 (6F, m), −121.1 (6F, m), −119.7 (6F, m), −107.2 (6F, m) −79.9 (9F, m).

bis-(Heptadecafluorooctanesulfonyl)methane 4c, Hdf$_2$CH$_2$

To a cooled, 3–5° C., stirred solution of trimethylsilylmethyllithium (150 mL, 150 mmol, 1M solution in pentane) was added neat heptadecafluorooctanesulfonyl fluoride (20.7 mL, 75 mmol) dropwise, through 2.5 hours by means of a syringe pump. The mixture was then stirred by 60 hours whilst allowing to warm to room temperature, before being quenched by the addition of saturated aqueous sodium bicarbonate solution (150 mL). The resulting mixture was decanted into a separating funnel, leaving a brown 'sticky' solid in the reaction vessel, the pentane layer separated and the aqueous layer extracted with DCM (3×50 mL). The aqueous layer was then acidified, to pH 1, by the addition of concentrated HCl (ca 50 mL) and extracted with diethyl ether (3×50 mL). The reaction residue was then treated and forcibly mixed with, saturated aqueous sodium bicarbonate solution (100 mL) to give a cloudy suspension. The aqueous mixture was then acidified, to pH 1, by the addition of HCl (ca 30 mL) to give a slurry which was then extracted with diethyl ether (3×30 mL). The combined ethereal extracts were then dried over $MgSO_4$, filtered and concentrated in vacuo to give a brown solid which was then triturated with 40–60 P.E. DCM and diethyl ether to give 4c (10.5 g, 29%) as a powdery white solid; $\delta_H$ (250 MHz, $CD_3COCD_3$) 5.55 (br s, C$\underline{H}_2$); $\delta_C$ (100 MHz, DMSO-$d_6$) 59.0 [s, $(C_8F_{17}SO_2)_3\underline{C}H_2$], 107.4–120.9 [m, ($\underline{C}_7F_{17}SO_2)_3CH_2$]; $\delta_F$ (250 MHz, $CD_3COCD_3$) −126.2 (4F, m), −122.7 (4F, m), −121.7 (12F, m), −119.6 (4F, m), −113.8 (4F, m), −81.2 (6F, m); m/z (FAB, −ve) 980 (M, 30%), 559 (100%).

Lithium tris-(Heptadecafluorohexanesulfonyl)methide 5c, Hdf$_3$CLi

To a cooled, −78° C., solution of 4c (980 mg, 1.0 mmol) in diethyl ether (30 mL) was added dropwise tert-butyllithium (1.25 mL, 2.1 mmol, 1.7M solution in pentane) and the reaction left to warm to −20° C. over 1 hour. The resulting solution was then cooled to −78° C. before heptadecafluorohexanesulfonyl fluoride (415 µL, 1.5 mmol) was added dropwise. The reaction mixture was allowed to warm to room temperature and stirred for 60 hours before being concentrated in vacuo and quenched with saturated aqueous sodium bicarbonate solution (50 mL). The aqueous layer was then acidified, to pH 1, by the addition of concentrated hydrochloric acid (ca 30 mL) before being extracted with diethyl ether (3×30 mL). The combined ethereal extracts were then concentrated in vacuo to yield a pale yellow solid which was taken into water (20 mL). A yellow/brown precipitate formed which was isolated by filtration and then washed with water (2×20 mL). The solid was then subjected to vacuum sublimation (170–180° C., 0.4 mbar) to remove starting material 4c. This allowed 5c to be isolated (220 mg, 15%) as a slightly impure dark brown glass; $\delta_F$ (250 MHz, DMSO-$d_6$) −125.4 (6F, m) −122.1 (6F, m), −121.2 (18F, m), −119.4 (6F, m), −107.3 (6F, m), −79.9 (9F, m); m/z (FAB, −ve) 1461 [(Hdf$_3$C)$^−$, 50%].

tris-(Tridecafluorobutanesulfonyl)methane 6c, Hdf$_3$CH

To 5c (90 mg, 0.06 mmol) was added concentrated $H_2SO_4$ (35 µL, ca 10 eq.). The resulting mixture was subjected to vacuum distillation (0.2 mbar, 150–160° C.) which generated a white oily solid. This was then dissolved in ether (5 mL) and water added (5 mL) followed by saturated aqueous barium chloride solution (7.5 mL). The ethereal layer was separated and the aqueous layer extracted with diethyl ether (2×10 mL) The combined ethereal extracts were then concentrated in vacuo and the organic residue subjected to vacuum distillation to yield 6c (63 mg, 72%) as a colourless oil which solidified upon standing; $\delta_F$ (250 MHz, DMSO-$d_6$) −125.7 (6F, m), −122.4 (6F, m), −121.3 (18F, m), −119.9 (6F, m) −107.3 (6F, m), −80.3 (9F, m); m/z (FAB, −ve) 1462 (M, 100%).

Lithium tris-[(bis-Tridecafluorohexanesulfonyl) heptadecafluorooctanesulfonyl]methide 5d, (Tdf)$_2$HdfCLi To a cooled, −20° C., solution of 4b (1.56 g, 2.0 mmol) in diethyl ether (40 mL) was added dropwise tert-butyllithium (2.5 mL, 4.2 mmol, 1.7M solution in pentane) and the reaction left to stir at −20° C. for 1 hour, heptadecafluorooctanesulfonyl fluoride (826 µL, 3.0 mmol) was then added dropwise. The reaction mixture was stirred for 24 hours and allowed to warm to room temperature before being concentrated in vacuo and quenched with saturated aqueous sodium bicarbonate solution (100 mL). The aqueous layer was then acidified, to pH 1, by the addition of concentrated hydrochloric acid (ca 50 mL) before being extracted with diethyl ether (3×30 mL). The combined ethereal extracts were then concentrated in vacuo to yield a yellow oily solid which was taken into water (10 mL). A yellow/brown precipitate formed which was isolated by filtration and then washed with water (2×20 mL). Purification was then carried out by trituration with diethyl ether at −78° C. to yield 5d (1.24 mg, 49%) as a brown oily solid; $\delta_C$ (100 MHz, DMSO-$d_6$) 88.8 [s, RfSO$_2$)$_3$C], 107.4–120.9 [m, $\underline{C}_8F_{17}SO_2(\underline{C}_6F_{13}SO_2)_2C$]; (F (250 MHz, DMSO-$d_6$) −125.4 (6F, m), −122.1 (6F, m), −121.1 (10F, m), −119.7 (6F, m), −107.2 (6F, m), −80.0 (9F, m).

tris-[(bis-Tridecafluorohexanesulfonyl) heptadecafluorooctanesulfonyl]methane 6d, (Tdf)$_2$HdfCH To 5d (1.08 g, 0.85 mmol) was added concentrated H$_2$SO$_4$ (0.5 mL, ca 10 eq.). The resulting mixture was subjected to vacuum distillation (0.3 mbar, 160–170° C.) which generated a white oily solid. This was then dissolved in ether (10 mL) and water added (10 mL) followed by saturated aqueous barium chloride solution (15 mL). The ethereal layer was separated and the aqueous layer extracted with diethyl ether (2×10 mL). The combined ethereal extracts were then concentrated in vacuo and the organic residue subjected to vacuum distillation to yield 6d (1.05 g, 95%) as a pale brown oil which solidified upon standing; $\delta_F$ (250 MHz, DMSO-$d_6$) −125.6 (6F, m), −122.3 (6F, m), −121.3 (10F, m), −119.9 (6F, m), −107.3 (6F, m), −80.1 (9F, m).

B. METAL COMPLEX PREPARATIONS
General Procedure:

A suspension of Yb$_2$O$_3$ (1.05 eq.) and Rf$_3$CH (6 eq.) (wherein Rf's may be different) in water and ethanol was heated at reflux for 24 hours. The solution was then diluted with ethanol, filtered and concentrated in vacuo to give Yb(CRf$_3$)$_3$.XH$_2$O as a pale brown glass which was dried under high vacuum over 2 days.

Ytterbium (III) tris-(Nonafluorobutanesulfonyl)methide 7a, Yb(CNf$_3$)$_3$ 6a (431 mg, 0.5 mmol), water (0.25 mL), ethanol (0.25 and 2 mL), Yb$_2$O$_3$ (34.5 mg, 0.088 mmol). This gave 7a (441 mg, 96% based upon x=0); $v_{max}$ (thin film)/cm$^{-1}$ 3350–3500, 1630, 1378, 1351, 1238, 1214, 1162, 1142, 1124, 1029, 971, 873, 737; $\delta_F$ (250 MHz, DMSO-$d_6$) −124.9 (18F, m), −120.6 (18F, m), −107.3 (18F, m), −79.8 (27F, m).

Ytterbium (III) tris-(Tridecafluorohexanesulfonyl)methide 7b, Yb(CTdf$_3$)$_3$ 6b (581 mg, 0.5 mmol), water (0.3 mL), ethanol (0.2 and 2 mL), Yb$_2$O$_3$ (34.5 mg, 0.088 mmol). This gave 7b (610 mg, 100% based upon x=0).

Ytterbium (III) tris-[(bis-Tridecafluorohexanesulfonyl) heptadecafluorooctanesulfonyl]methide 7c, Yb[C(Tdf$_3$)$_2$Hdf]$_3$ 6d (252 mg, 0.2 mmol), water (0.3 mL), ethanol (0.3 and 2 mL), Yb$_2$O$_3$ (13.8 mg, 0.035 mmol). This gave 7c (258 mg, 98% based upon x=0); $\delta_F$ (250 MHz, DMSO-$d_6$) −125.2 (18F, m), −122.0 (18F, m), −121.1 (30F, m), −119.6 (18F, m), −107.1 (18F, m), −79.7 (27F, m).

C. OTHER PROCESS EXAMPLES
Hydroxyalkylation Using Ethyl Glyoxalate

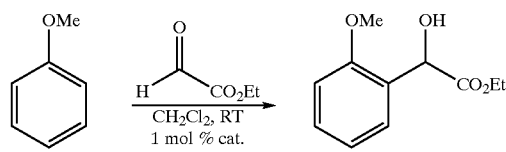

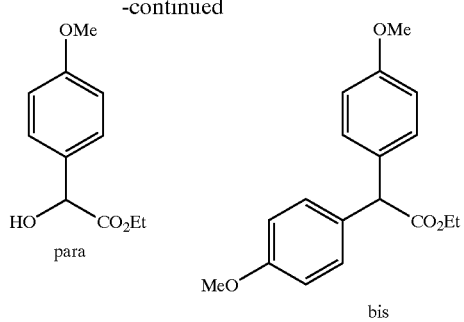

To a solution of anisole (163 μL, 1.5 mmol) and Yb(CNf$_3$)$_3$ (41 mg, 0.015 mmol, 1 mol %) in dry CH$_2$Cl$_2$ was added ethyl glyoxylate (446 μL, 5000 solution in toluene, 2.25 mmol) and stirred for 48 hours. The solvent was removed under reduced pressure and the mixture chromatographed to give the bis-adduct as a colourless oil: IR (thin film; NaCl plate) 2958, 2938, 2837, 1730 vs, 1611, 1584, 1512 cm$^{-1}$ $\delta_H$ (300 MHz, CDCl$_3$) 7.25 (4H, d, J=8.7 Hz, Ar—H×4), 6.88 (4H, d, J=8.7 Hz, Ar—H×4), 4.94 (1H, s, Ar$_2$CH), 4.23 (2H, q, J=7.1 Hz, CO$_2$CH$_2$), 3.81 (6H, s, OMe×2) 1.28 (3H, t, J=7.1 Hz, CO$_2$CH$_2$CH$_3$); $\delta_C$ (75 MHz, CDCl$_3$) 173.1, 158.8, 131.3, 129.6, 114.0, 61.0, 55.5, 55.3, 14.2, MS 300 (M$^+$), 227. Analytical data for the mono-adduct (para) were obtained from the reaction run using scandium triflate as the catalyst: IR (thin film; NaCl plate) 3480 br, 2982, 1736 vs, 1612, 1587, 1513 cm$^{-1}$ $\delta_H$ (300 MHz, CDCl$_3$) 7.34 (2H, d, J=8.7 Hz, Ar—H×2), 6.90 (2H, d, J=8.7 Hz, Ar—H×2), 5.12 (1H, s, CHOH), 4.32–4.11 (2H, m, CO$_2$CH$_2$), 3.81 (3H, s, OMe), 1.24 (3H, t, J=7.1 Hz, CO$_2$CH$_3$); $\delta_C$ (75 MHz, CDCl$_3$) 173.9 (C=O), 159.7, 130.7, 127.9, 114.0, 72.5, 62.1, 55.3, 14.1; MS 210 (M$^+$), 137.

Intramolecular Hydroxyalkylation (Isochroman Formation)

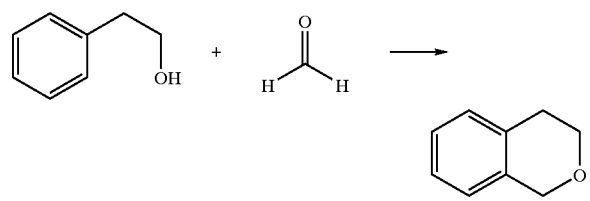

To a solution of phenethyl alcohol (122 mg, 1.0 mmol) in glacial acetic acid (2 mL) was added formaldehyde (40% in water, 100 μl, 1.5 mmol) and Yb(CNf$_3$)$_3$ (276 mg, 0.1 mmol, 10 mol %). The mixture was stirred at reflux for 18 hours. The mixture was allowed to cool, diluted with CH$_2$Cl$_2$, washed with water, aqueous sodium hydrogen carbonate solution, and brine, dried over MgSO$_4$, filtered and evaporated. Chromatography (3:1 PE:Et$_2$O) gave isochroman (54 mg, 40%) as a colourless oil: IR (thin film; NaCl plate) 2929, 2851, 1605, 1585 cm$^{-1}$; $\delta_H$ (300 MHz, CDCl$_3$) 7.23–7.14 (3H, m, Ar—H×3), 7.04–7.00 (1H, m, Ar—H), 4.82 (2H, s, ArCH$_2$O), 4.04 (2H, t, J=5.7 Hz, ArCH$_2$OCH$_2$), 2.90 (2H, t, J=5.7 Hz, ArCH$_2$CH$_2$); $\delta_C$ (75 MHz, CDCl$_3$) 135.0, 133.3, 129.0, 126.4, 126.0, 124.4, 68.0, 65.4, 28.4; MS 134 (M$^+$), 104, 77, 51.

Intramolecular Carbonyl ene Cyclisation

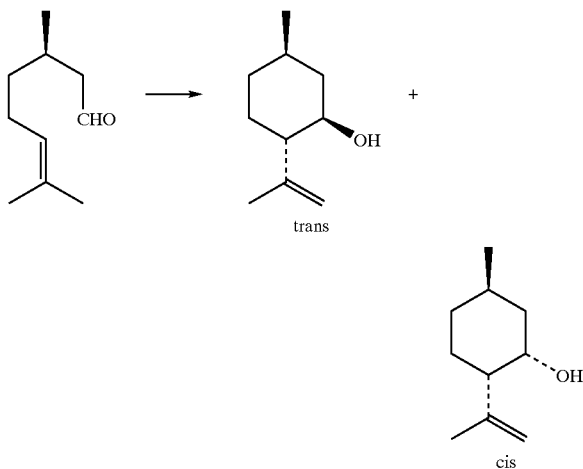

To a cooled solution (−78° C.) of Yb(CNf$_3$)$_3$ (276 mg, 0.1 mmol, 10 mol %) in CH$_2$Cl$_2$ (20 mL) was added freshly distilled citronellal (180 μl, 1.0 mmol). The reaction was stirred at −78° C. for 3 hours. GC monitoring indicated that all the aldehyde had reacted. The mixture was diluted with CH$_2$Cl$_2$, washed with water, dried over MgSO$_4$, evaporated and chromatographed (7:3 PE:Et$_2$O) to give isopugelone (62 mg, 40%) as a colourless oil (trans isomer): IR (thin film; NaCl plate) 3410 br, 1950, 2924, 2869, 1645 cm$^{-1}$; δ$_H$ (300 MHz, CDCl$_3$) 4.88 (1H, br s, C=CHH), 4.84 (1H brs, C=CHH), 3.45 (1H, ddd, J=14.6, 10.4, 4.3 Hz, CHOH) 2.05–1.831. (3H, m), 1.72–1.64 (5H, m) 1.59–1.47 (1H, m) 1.42–1.20 (1H, m) 1.10–0.82 (5H, m); δ$_C$ (75 MHz, CDCl$_3$), 146.7, 112.9, 70.4, 54.1, 42.7, 34.3, 31.5, 29.7, 22.3, 19.2; MS 154 (M$^+$), 136, 121, 81, 67, 55. The minor (cis) isomer (13 mg, 8%) could also be isolated as a colourless oil: δ$_H$ (300 MHz, CDCl$_3$) 4.97 (1H, br s, C=CCHH), 4.80 (1H br s, C=CHH), 4.00 (19 br s, CHOH), 2.01–0.85 (15H, m); δ$_C$ (75 MHz, CDCl$_3$ 147.4, 111.3, 66.3, 48.4, 40.9, 34.7, 25.8, 24.0, 22.8, 22.3. MS 154 (M$^+$), 139, 136, 121, 95, 81, 59.

What is claimed is:

1. In a process involving a catalyzed carbon-carbon bond formation, the improvement wherein the catalyst is a fluorosulfonylmethide compound represented by the formula I:

$$M[C(SO_2R^1)_{3-(m+q)}(SO_2R^2)_m(SO_2R^3)_q]_x$$

where
M is H, Sc, Y, La, Ce, Pr, Nd, Sm, Eu, Gd, Tb, Dy, Ho, Er, Tm, Yb, Lu, Zr, Hf, Th, Nb, Ta, U, Bi, Al, Ga, In or Tl
x is the common oxidation state of a said metal M
R$^1$, R$^2$ and R$^3$ are perfluorinated or polyfluorinated hydrocarbon, ether or amine moieties or mixtures thereof
and m+q=0, 1 2 or 3 (m and q being zero or integers).

2. Process according to claim 1 wherein R$^1$, R$^2$ and R$^3$ are perfluorinated hydrocarbon moieties.

3. Process according to claim 2 wherein m and q are zero and R$^1$ is C$_4$F$_9$, C$_6$F$_{13}$ or C$_8$F$_{17}$.

4. Process according to claim 2 wherein m is 1, q is zero, R$^2$ or R$^1$ is C$_6$F$_{13}$ and R$^1$ or R$^2$ is C$_8$F$_{17}$.

5. Process according to claim 1 wherein M is a lanthanide metal or Hafnium.

6. A process for catalyzed C—C bond formation according to claim 1 wherein said compound of the formula I is present in a catalytic quantity.

7. A process according to claim 6 wherein the catalytic quantity is 10 mole % or less, based on the substrate.

8. A process according to claim 7 wherein the catalytic quantity is 1 mole % or less, based on the substrate.

9. A process according to claim 8 wherein the catalytic quantity is 0.1 mole % or less, based on the substrate.

10. A process according to claim 6 wherein the reaction is carried out in a solvent.

11. A process according to claim 6 wherein the reaction is carried out in the presence of a fluorous medium.

12. A process according to claim 11 wherein the fluorous medium is part of a fluorous biphasic system and the compound of formula I is preferentially soluble in the fluorous medium.

13. A process according to claim 6 which is carried out in the absence of solvent.

14. A process according to claim 13 including subsequent separation of the said compound into a fluorous medium.

15. A process according to claim 5 which involves a Friedel-Crafts reaction.

16. A compound of the formula I

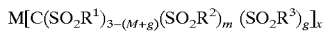

where
M is H, Sc, La, Ce, Pr, Nd, Sm, Eu, Gd, Tb, Dy, Ho, Er, Tm, Yb, Lu, Zr, Hf, Th, Nb, Ta, U, Bi, Al, Ga, In or Tl
x is the common oxidation state of a said metal M
R$^1$, R$^2$ and R$^3$ are perfluorinated or polyfluorinated hydrocarbon, ether or amine moieties or mixtures thereof
and m+g=0, 1, 2 or 3 (m and q being zero or integers) with the exclusion of compounds where M is H, Yb or Sc, and m and q are zero and R$^1$=CF$_3$.

17. A compound of the formula I

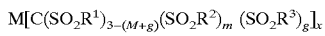

where
M is H, Sc, La, Ce, Pr, Nd, Sm, Eu, Gd, Tb, Dy, Ho, Er, Tm, Yb, Lu, Zr, Hf, Th, Nb, Ta, U, Bi, Al, Ga, In or Tl
x is the common oxidation state of a said metal M
R$^1$, R$^2$ and R$^3$ are perfluorinated or polyfluorinated hydrocarbon, ether or amine moieties or mixtures thereof
and m+g=0, 1, 2 or 3 (m and g being zero or integers) with the further proviso that R$^1$, R$^2$ and R$^3$ and perfluorinated hydrocarbon moieties, and m and g are zero and R$_1$ is C$_4$F$_9$, C$_6$F$_{13}$ or C$_8$F$_{17}$.

18. A mixed-ligand compound of the formula I

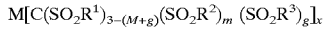

where
M is H, Sc, La, Ce, Pr, Nd, Sm, Eu, Gd, Tb, Dy, Ho, Er, Tm, Yb, Lu, Zr, Hf, Th, Nb, Ta, U, Bi, Al, Ga, In or Tl
x is the common oxidation state of a said metal M
R$^1$, R$^2$ and R$^3$ are perfluorinated or polyfluorinated hydrocarbon, ether or amine moieties or mixtures thereof
and m+g=0, 1, 2 or 3 (m and g being zero or integers) with the further proviso that R$^1$, R$^2$ and R$^3$ and perfluorinated hydrocarbon moieties, and m is 1, g is zero, R$^2$ or R$^1$ is C$_6$F$_{13}$ and R$^1$ or R$^2$ is C$_8$F$_{17}$.

19. A process for the preparation of a compound as claimed in claim 16 which includes the preparation of an alkali metal salt of fluorosulfonylmethide compound of the formula I (with the said exclusion), separating the same alkali metal salt from aqueous solution, acidification of the separated compound to the free methide and optionally treatment with an oxide of a said metal M of formula I.

20. A process for the preparation of a compound as claimed in claim 17 or claim 18 which includes the preparation of $(C_nF_{2n+1}SO_2)_3CM^1$ wherein n is an integer or a mixture of integers and $M^1$ is an alkali metal, separating $(C_nF_{2n+1}SO_2)_3CM^1$ from aqueous solution where M' is the same alkali metal, with subsequent acidification of the separated compound to $(C_nF_{2n+1}SO_2)_3CH$ and optionally treatment with an oxide of a said metal M of formula I.

21. A process according to claim 19 or claim 20 wherein $M^1$ is lithium.

22. A process according to claim 19, claim 20 or claim 21 wherein the separation is initially as an oil with subsequent solidification.

* * * * *

UNITED STATES PATENT AND TRADEMARK OFFICE
CERTIFICATE OF CORRECTION

PATENT NO. : 6,664,380 B1
DATED : December 16, 2003
INVENTOR(S) : Anthony Gerard Martin Barrett et al.

It is certified that error appears in the above-identified patent and that said Letters Patent is hereby corrected as shown below:

<u>Title page,</u>
Item [22], delete "Mar. 31, 2000" and insert -- Aug. 9, 2000 --.

Signed and Sealed this

First Day of June, 2004

JON W. DUDAS
*Acting Director of the United States Patent and Trademark Office*